(12) United States Patent
Ellis et al.

(10) Patent No.: US 6,990,220 B2
(45) Date of Patent: Jan. 24, 2006

(54) APPARATUSES AND METHODS FOR SURGICAL NAVIGATION

(75) Inventors: Randy E. Ellis, Kingston (CA); Thomas J. Radcliffe, Kingston (CA)

(73) Assignee: IGO Technologies Inc., Kingston (CA)

( * ) Notice: Subject to any disclaimer, the term of this patent is extended or adjusted under 35 U.S.C. 154(b) by 895 days.

(21) Appl. No.: 09/879,987

(22) Filed: Jun. 14, 2001

(65) Prior Publication Data

US 2002/0191814 A1 Dec. 19, 2002

(51) Int. Cl.
*G06K 9/00* (2006.01)

(52) U.S. Cl. .............. 382/128; 382/285; 600/109; 128/922

(58) Field of Classification Search ............ 382/103, 382/128, 132; 128/922; 600/443, 463, 109, 600/424; 606/80; 378/205; 342/55; 348/169
See application file for complete search history.

(56) References Cited

U.S. PATENT DOCUMENTS

| | | | |
|---|---|---|---|
| 5,251,127 A | | 10/1993 | Raab |
| 5,305,203 A | | 4/1994 | Raab |
| 5,748,767 A | | 5/1998 | Raab |
| 5,772,594 A | | 6/1998 | Barrick |
| 5,951,475 A | * | 9/1999 | Gueziec et al. ............ 600/425 |
| 6,129,668 A | * | 10/2000 | Haynor et al. ............. 600/424 |
| 6,470,207 B1 | * | 10/2002 | Simon et al. .............. 600/426 |
| 6,477,400 B1 | * | 11/2002 | Barrick ..................... 600/426 |
| 6,529,758 B2 | * | 3/2003 | Shahidi ..................... 600/407 |
| 6,546,279 B1 | * | 4/2003 | Bova et al. ................ 600/429 |
| 6,636,757 B1 | * | 10/2003 | Jascob et al. ............. 600/424 |
| 6,640,127 B1 | * | 10/2003 | Kosaka et al. ............ 600/426 |
| 2001/0027272 A1 | * | 10/2001 | Saito et al. ............... 600/426 |
| 2002/0172328 A1 | * | 11/2002 | Dekel ....................... 378/205 |
| 2002/0193800 A1 | * | 12/2002 | Kienzle et al. ............. 606/80 |

(Continued)

OTHER PUBLICATIONS

Crowl, Adam C. et al, Closed Reduction and Percutaneous Fixation of Anterior Column Acetabular Fractures, Computer Aided Surgery, 2002, 7:169–178, Wiley InterScience, online.

Suhm, N., Surgical Navigation Based on Fluoroscopy—Clinical Application for Computer–Assisted Distal Locking of Intramedullary Implants, Cimputer Aided Surgery, 2000, 5:391–400, Wiley–Liss, Inc.

Hofstetter, R., Slomczykowski, M., Sati, M., and Nolte, L.-P., "Fluoroscopy as an Imaging Means for Computer–Assisted Surgical Navigation", Computer Aided Surgery, 4:65–76 (May 3, 1999), pp. 65–76.

*Primary Examiner*—Bhavesh M. Mehta
*Assistant Examiner*—Barry Choobin

(57) ABSTRACT

Imaging, object tracking, integration apparatus 100 has tracking system 1, imaging system 3, communication system 5 and integration system 7. Tracking system 1 locates objects in 3-dimensions and determines respective poses. Imaging system 3 acquires object images. Integration system 7 correlates 3-dimensional poses. User communication system 5 provides information, such as images, sounds, or control signals to the user or other automated systems. Image acquisition techniques include X-ray imaging and ultrasound imaging. Images can be acquired from digital files. Imaging system 3 creates a calibrated, geometrically corrected two-dimensional image 110, 210. Correlation system 7 can receive instructions from a practitioner to create, destroy, and edit the properties of a guard. Communications system 5 displays images and calculations to a practitioner, such as a surgeon. Methods can determine geometrical relations between guards and/or present to a practitioner projections of forms of guards.

50 Claims, 8 Drawing Sheets

U.S. PATENT DOCUMENTS

| | | | |
|---|---|---|---|
| 2003/0028091 A1 * | 2/2003 | Simon et al. | 600/407 |
| 2003/0043969 A1 * | 3/2003 | Menhardt | 378/210 |
| 2003/0130576 A1 * | 7/2003 | Seeley et al. | 600/426 |
| 2003/0163040 A1 * | 8/2003 | Gildenberg | 600/429 |
| 2003/0208116 A1 * | 11/2003 | Liang et al. | 600/407 |
| 2003/0208122 A1 * | 11/2003 | Melkent et al. | 600/426 |
| 2004/0096091 A1 * | 5/2004 | Bascle et al. | 382/132 |
| 2004/0116803 A1 * | 6/2004 | Jascob et al. | 600/424 |
| 2004/0181149 A1 * | 9/2004 | Langlotz et al. | 600/431 |

\* cited by examiner

APPARATUSES AND METHODS FOR SURGICAL NAVIGATION

FIELD OF THE INVENTION

The invention is related to the inference, representation, and manipulation of three-dimensional geometry derived from two or more two-dimensional images.

BACKGROUND OF THE INVENTION

Many current medical, manufacturing and inspection practices rely on relating three-dimensional geometry to two-dimensional projection or tomographic images. An example of a projection image is a plain radiograph, in which electromagnetic energy transmitted and refracted through or by physical objects, until film or another process, such as a digital process, creates an image. Examples of tomographic imaging technologies include, but are not limited to, computed tomography, magnetic resonance imaging, ultrasound imaging, positron emission tomography, and single photon emission computed tomography. An example of a tomographic image is an ultrasound image, in which acoustic energy transmitted and refracted through or by physical objects, until a process, such as a digital process, creates an image.

An image is information that represents a two-dimensional projection as carried by an appropriate medium. An image file stored on a floppy disk, hard disk or other storage medium is an image, as is an x-ray film. An image can be captured by processes such as beam intensity absorption, phase distortion, and frequency modulation, among many possible physical processes. The energy used to create the image can be electromagnetic, electric, magnetic, acoustic, or any other energy.

Three-dimensional geometrical knowledge derived from two-dimensional images can be used for many purposes, including diagnosis of state of health, guidance of objects that are tracked relative to the derived three-dimensional geometry, and quality control. In some of these applications, such as inferring the safe volume for drilling a bone, expert knowledge of the objects being imaged is required to infer the three-dimensional geometrical structure. For the purposes of object guidance a means of representing the derived geometry is required, as is the ability to reference the derived geometry to a coordinate frame in which the pose(s) of the object(s) that are tracked are known. A deficiency in existing use of two-dimensional images is that the derivation of three-dimensional geometry, and useful inferences therefrom, rely principally on the skill of the observer and the derivations and uses are not easily computed by automatic means.

One common use of three-dimensional geometry derived from multiple two-dimensional images is the use of fluoroscopic imaging in orthopaedic surgery. In this case, one or more two-dimensional fluoroscopic images are taken for the purpose of inferring the patient's anatomy in three dimensions; the mental image of the anatomy can be used to determine the placement of cuts, drill-holes and other anatomical modifications that a surgeon may wish to carry out. A plurality of two-dimensional images are often taken during the course of drilling or cutting the patient's anatomy to ensure that the drilling, cutting or other process is following the intended course and is not in danger of affecting any but the intended anatomical structures. At least two problems arise from taking a plurality of fluoroscopic images during the course of operating on a patient. The patient and the surgical team are exposed to additional X-ray radiation beyond the radiation needed to create the initial image. The fluoroscope can physically obstruct the surgeon who is performing the operation.

Methods exist to alleviate the two problems of additional radiation and physical obstruction. For example, the patient's anatomy can be tracked by physically attaching an object that can be detected by a computer via a tracking means and attaching a distinct object to the fluoroscope that can also be detected by a computer via a tracking means. The pose of the X-ray source of the fluoroscope with respect to the imaging system of the fluoroscope can be determined prior to image creation or after image creation. Thereafter, if a tool, such as a surgical instrument, has attached to it a distinct object that can also be detected by a computer via a tracking means and that is attached to the tool in a known manner, then an artificial image of the tool as it would appear in the fluoroscopic image of the patient can be computed. Typically but not necessarily, the artificial image of the tool is generated by determining how specific known points of the tool would appear on the fluoroscopic image had the tool been present during the physical process of creating the image, and superimposing a simple two-dimensional geometrical object on the actual fluoroscopic image. Such a method and apparatus permits a practitioner, who is a surgeon or some other user of the fluoroscope, to create one or more images of the patient's anatomy, remove the fluoroscope from the immediate vicinity of the practitioner and the patient, and observe the artificial image superimposed on the real fluoroscopic image.

At least one deficiency of the above method is that three-dimensional guidance from multiple two-dimensional images is inherently difficult because multiple two-dimensional images may be misinterpreted. An example of this problem in projection imaging is shown in the attached figure: in both two-dimensional images the tool appears to be inside the sphere, when the tool has actually penetrated through the sphere's surface. Alternate apparatuses and methods for the inferring, representing and manipulating three-dimensional geometric objects from multiple two-dimensional images are desirable.

As an illustrative example, consider the case of an orthopedic surgeon who seeks to repair a fractured hip by drilling the proximal femur from the greater trochanter through the femoral neck into the femoral head. A skilled practitioner might observe an image captured at one angle with respect to the principal axis of the femur and observe an image that is captured at some other angle with respect to the principal axis of the femur. By drawing on knowledge of anatomy, the practitioner might determine how to position a drill so as to pierce the desired anatomy and not pierce other anatomy. The observation of other fluoroscopic images, captured as the drill progresses through the anatomy, aids a skilled practitioner in fluoroscopically guided drilling. The practitioner would require considerable prior understanding of normal and pathological anatomy, and might be inconvenienced by the physical presence of the fluoroscope during the drilling process.

A practitioner who takes great advantage of existing systems might cause the creation of the two aforementioned images by means of a computer system that can create, from each image, a calibrated, geometrically corrected image. The computer system might then track the drill and a bone of the patient by real-time tracking and determine the pose of the drill with respect to an anatomical coordinate frame. The computer system might further superimpose on the calibrated, geometrically corrected image a point, line, or other two-dimensional geometrical shape that provides the practitioner with an indication of where the drill might have appeared in the calibrated, geometrically corrected image had the drill been physically present during the physical process of image creation. Thus, the practitioner might observe the computer-generated images and observe where the drill might be with respect to the femoral anatomy. Such a practitioner would not be exposed to X-ray radiation emitted by the fluoroscope during the process of image creation, and could have the fluoroscope removed from the immediate vicinity so as not to be inconvenienced by the physical presence of the fluoroscope during the drilling process.

Due to projective geometry, the actual three-dimensional relationship of three-dimensional objects may not be apparent from two-dimensional projective or tomographic images. A mathematically simple example can be constructed by considering a unit sphere centered at the origin of a coordinate frame, a vector directed from the origin in the direction (1,1,1) with length (2/3,2/3,2/3), an orthographic projection of said unit sphere and said vector to the XY plane of said coordinate frame, and an orthographic projection of said unit sphere and said vector to the XZ plane of said coordinate frame. In the XY projection the tip of said vector will appear to lie within the circle that is the projection of said sphere, and similarly for the XZ projection. Simple calculation shows that the length of said vector exceeds the radius of said sphere, so although the projections suggest that the vector lies entirely within the sphere such is not the case. For said examples of a skilled practitioner using only fluoroscopic images and of a skilled practitioner using computer-generated images, it is possible that the practitioner might pierce the femoral head and thereby cause vile undesired consequences to the health of the patient. Similar problems occur with tomographic images because two-dimensional projection images and two-dimensional tomographic images are not adequate representations of three-dimensional geometry.

SUMMARY OF THE INVENTION

In an aspect the invention provides a method of surgical navigation. The method acquires a first image of part of a patient on a first surface of creation wherein the image is captured using a first imaging system, acquires a first pose of the part of the patient when the part of the patient is in substantially the same pose that the part is in when the first image is captured, acquires a first pose of the surface of creation with respect to the part of the patient when the part of the patient and the first imaging system are in substantially the same pose with respect to one another that the part of the patient and the first image are in when the first image is captured, and sets a first pose of a virtual guard with respect to the part of the patient as if the part of the patient is positioned with respect to the first virtual surface of creation in the same geometric relationship that the part of the patient has with respect to the first surface of creation.

The method may acquire a second image of the part of the patient on a second surface of creation wherein the image is captured using a second imaging system, acquire a second pose of the part of the patient when the part of the patient is in substantially the same pose that the part is in when the second image is captured, acquire a second pose of the second surface of creation with respect to the part of the patient when the part of the patient and the second imaging system are in substantially the same pose with respect to one another that the part of the patient and the second image are in when the second image is captured, set a second pose of a second virtual surface of creation with respect to the part of the patient as if the part of the patient is positioned with respect to the second virtual surface of creation in the same geometric relationship that the part of the patient has with respect to the second surface of creation, and set a second pose of the virtual guard with respect to the second virtual surface of creation.

The method may employ a first imaging system that is a projective imaging system.

The method may acquire a pose of the first imaging system with respect to the first surface of creation, set a first pose of a first virtual imaging system with respect to the first virtual surface of creation, and project a first virtual image of the virtual guard onto the first virtual surface of creation using the first virtual imaging system.

The method may employ a second imaging system that is a projective imaging system.

The method may acquire a pose of the second imaging system with respect to the second surface of creation, set a second pose of a second virtual imaging system with respect to the second virtual surface of creation, and project a second virtual image of the virtual guard onto the second virtual surface of creation using the second virtual imaging system.

In an aspect the invention provides a method of surgical navigation. The method acquires a first image of part of a patient on a first surface of creation wherein the image is captured using a first imaging system, acquires a first pose of the part of the patient when the part of the patient is in substantially the same pose that the part is in when the first image is captured, acquires a first pose of the surface of creation with respect to the part of the patient when the part of the patient and the first imaging system are in substantially the same pose with respect to one another that the part of the patient and the first image are in when the first image is captured, acquire a first pose of a tool, and sets a first pose of a virtual form of the tool with respect to the part of the patient as if the part of the patient is positioned with respect to the first virtual surface of creation in the same geometric relationship that the part of the patient has with respect to the first surface of creation.

The method may employ a first imaging system that is a projective imaging system.

The method may acquire a pose of the first imaging system with respect to the first surface of creation, set a first pose of a first virtual imaging system with respect to the first virtual surface of creation, and project a first virtual image of the virtual form of the tool onto the first virtual surface of creation using the first virtual imaging system.

In an aspect the invention provides a method of surgical navigation. The method acquires a first image of part of a patient on a first surface of creation wherein the image is captured using a first imaging system, acquires a first pose of the part of the patient when the part of the patient is in substantially the same pose that the part is in when the first image is captured, acquires a first pose of the surface of creation with respect to the part of the patient when the part of the patient and the first imaging system are in substantially the same pose with respect to one another that the part of the patient and the first image are in when the first image is captured, sets a first pose of a first virtual surface of creation with respect to the part of the patient as if the part of the patient is positioned with respect to the first virtual surface of creation in the same geometric relationship that the part of the patient has with respect to the first surface of creation, sets a first pose of a first virtual guard with respect to a first virtual surface of creation, acquires a first pose of a tool, and sets a first pose of a virtual form of the tool with respect to the part of the patient as if the part of the patient is positioned with respect to the first virtual surface of creation in the same geometric relationship that the part of the patient has with respect to the first surface of creation.

The method may employ a first imaging system that is a projective imaging system.

The method may acquire a pose of the first imaging system with respect to the first surface of creation, set a first pose of a first virtual imaging system with respect to the first virtual surface of creation, project a first virtual image of the virtual form of the tool onto the first virtual surface of creation using the first virtual imaging system.

The method may acquire a pose of the first imaging system with respect to the first surface of creation, set a first pose of a first virtual imaging system with respect to the first virtual surface of creation, project a first virtual image of the virtual guard onto the first virtual surface of creation using the first virtual imaging system.

The method may acquire a pose of the tool on an ongoing basis, acquire a pose of the part of the patient on an ongoing basis, reset the first pose of the virtual form of the tool on an ongoing basis to compensate for changes of the pose of the tool with respect to the part of the patient.

The methods may store the acquired images on a computer readable medium after the images are acquired. The methods may display each acquired image together with one or more of the virtual images captured from the same projected perspective.

The methods may display one or more virtual images, where multiple virtual images are captured from the same projected perspective, without displaying an acquired image. The methods may act upon a plurality of images of the part of the patient. The methods may act upon a plurality of guards. The methods may act upon a plurality of tools.

The methods may calculate relative pose information of a tool and another tool.

The methods may calculate relative pose information of the tool and the guard.

The methods may display the relative pose information by displaying images of the tool and guard. The methods may display the relative pose information is audibly.

The methods may display the relative pose information visually in the form of numerical data. The methods may display the relative pose information graphically. The methods may calculate relative pose information of one or more tools and one or more guards.

The methods may act upon a tool selected from a group consisting of drills, probes, saws, guides, probes, or another physical objects that a practitioner can directly or indirectly manipulate. The methods may act upon guards selected from a group consisting of drill holes, probe holes, saw cuts, guide holes, probe holes, or another three-dimensional computer representation of a geometrical entity.

The methods may act upon images acquired by capturing the images from the patient using an imaging system. The imaging system may be an X-ray system. The imaging system may be an ultrasound system.

The images may be acquired by retrieving from a computer readable file previously captured images. Poses may be acquired by tracking poses using a tracking system.

The tracking system may transmit signals from items and receive transmitted signals at a sensor, and the tracking system may determine poses from the received transmitted signals.

Poses may be acquired by retrieving them from a computer readable file of previously tracked poses.

Images may be geometrically corrected to represent substantially a product of projective geometry only, and not of artifacts or distortions introduced by an imaging system, whether calculated from geometry or calculated by processing an image derived from an imaging system.

In an aspect the invention provides an apparatus for use in surgical navigation. The apparatus includes a tracking system for tracking objects, an imaging system for acquiring 2-dimensional images of objects, a communication system for receiving input from and providing output to a user, an integration system for correlating images acquired at different times or using different means of acquisition, a computing platform, and computer program means on computer readable media for use on the computer platform. The computer program means includes instructions to carry out the steps of one of the methods using the tracking system, imaging system, communication system and integration system.

The apparatus may include, in the tracking system, one or more transmitters on each object for transmitting a signal, and one or more sensors for receiving transmitted signals, the transmitter determining a pose of an object using the received transmitted signals.

In an aspect the inventions provides a computer program on a computer readable medium for use on a computer platform in association with a tracking system for tracking objects, an imaging system for acquiring 2-dimensional images of objects, a communication system for receiving input from and providing output to a user, an integration system for correlating images acquired at different times or using different means of acquisition. The computer program includes instructions to carry out the steps of one of the methods using the tracking system, imaging system, communication system and integration system.

In an aspect the invention provides an apparatus for use in surgical navigation. The apparatus includes a tracking system for tracking objects, an imaging system for acquiring 2-dimensional images of objects, an integration system for correlating images acquired at different times or using different means of acquisition, wherein the imaging system acquires a first image of part of a patient on a first surface of creation, the image is captured using a first imaging system, the tracking system acquires a first pose of the part of the patient when the part of the patient is in substantially the same pose that the part is in when the first image is captured, the tracking system acquires a first pose of the first imaging system with respect to the part of the patient when the part of the patient is in substantially the same pose that the part is in when the first image is captured, the tracking system acquires a first pose of the surface of creation with respect to the part of the patient when the part of the patient and the first imaging system are in substantially the same pose with respect to one another that the part of the patient and the first image are in when the first image is captured, the integration system sets a first pose of a first virtual imaging system with respect to a first virtual surface of creation, the integration system sets a first pose of a virtual guard with respect to the part of the patient as if the part of the patient is positioned with respect to the first virtual imaging system and the first virtual surface of creation in the same geometric relationship that the part of the patient has with respect to the first imaging system and the first surface of creation, the integration system projects a first virtual image of the guard onto the first virtual surface of creation using the first virtual imaging system.

In an aspect the invention provides an apparatus for use in surgical navigation in association with an acquired first image of part of a patient on a first surface of creation, the image captured using a first imaging system; an acquired first pose of the part of the patient when the part of the patient is in substantially the same pose that the part is in when the first image is captured, an acquired first pose of the first imaging system with respect to the part of the patient when the part of the patient is in substantially the same pose that the part is in when the first image is captured, and an acquired first pose of the surface of creation with respect to the part of the patient when the part of the patient and the first imaging system are in substantially the same pose with respect to one another that the part of the patient and the first image are in when the first image is captured. The apparatus includes an integration system for correlating images acquired at different times or using different means of acquisition, wherein the integration system sets a first pose of a first virtual imaging system with respect to a first virtual surface of creation, wherein the integration system sets a first pose of a virtual guard with respect to the part of the patient as if the part of the patient is positioned with respect to the first virtual imaging system and the first virtual surface of creation in the same geometric relationship that the part of the patient has with respect to the first imaging system and the first surface of creation, and wherein the integration system projects a first virtual image of the guard onto the first virtual surface of creation using the first virtual imaging system.

In an aspect the invention provides an apparatus for use in surgical navigation in association with an acquired first image of part of a patient on a first surface of creation, the image captured using a first imaging system; an acquired first pose of the part of the patient when the part of the patient is in substantially the same pose that the part is in when the first image is captured, an acquired first pose of the first imaging system with respect to the part of the patient when the part of the patient is in substantially the same pose that the part is in when the first image is captured, an acquired first pose of the surface of creation with respect to the part of the patient when the part of the patient and the first imaging system are in substantially the same pose with respect to one another that the part of the patient and the first image are in when the first image is captured, and an acquired first pose of a tool. The apparatus includes an integration system for correlating images acquired at different times or using different means of acquisition, wherein the integration system sets a first pose of a first virtual imaging system with respect to a first virtual surface of creation,
  wherein the integration system sets a first pose of a virtual form of the tool with respect to the part of the patient as if the part of the patient is positioned with respect to the first virtual imaging system and the first virtual surface of creation in the same geometric relationship that the part of the patient has with respect to the first imaging system and the first surface of creation, and wherein the integration system projects a first virtual image of the tool onto the first virtual surface of creation using the first virtual imaging system.

In an aspect the invention provides an apparatus for use in surgical navigation in association with an acquired first image of part of a patient on a first surface of creation, the image captured using a first imaging system; an acquired first pose of the part of the patient when the part of the patient is in substantially the same pose that the part is in when the first image is captured, an acquired first pose of the first imaging system with respect to the part of the patient when the part of the patient is in substantially the same pose that the part is in when the first image is captured, and an acquired first pose of the surface of creation with respect to the part of the patient when the part of the patient and the first imaging system are in substantially the same pose with respect to one another that the part of the patient and the first image are in when the first image is captured, and an acquired first pose of a tool. The apparatus includes an integration system for correlating images acquired at different times or using different means of acquisition, wherein the integration system sets a first pose of a first virtual imaging system with respect to a first virtual surface of creation, wherein the integration system sets a first pose of a virtual form of the tool with respect to the part of the patient as if the part of the patient is positioned with respect to the first virtual imaging system and the first virtual surface of creation in the same geometric relationship that the part of the patient has with respect to the first imaging system and the first surface of creation, wherein the integration system projects a first virtual image of the tool onto the first virtual surface of creation using the first virtual imaging system, wherein the integration system sets a first pose of a virtual guard with respect to the part of the patient as if the part of the patient is positioned with respect to the first virtual imaging system and the first virtual surface of creation in the same geometric relationship that the part of the patient has with respect to the first imaging system and the first surface of creation, and wherein the integration system projects a first virtual image of the guard onto the first virtual surface of creation using the first virtual imaging system.

BRIEF DESCRIPTION OF THE DRAWINGS

For a better understanding of the present invention and to show more were clearly how it may be carried into effect, reference will now be made, by way of example, to the accompanying drawings that show the preferred embodiment of the present invention and in which.

DETAILED DESCRIPTION OF THE PREFERRED EMBODIMENTS

Figure 1:
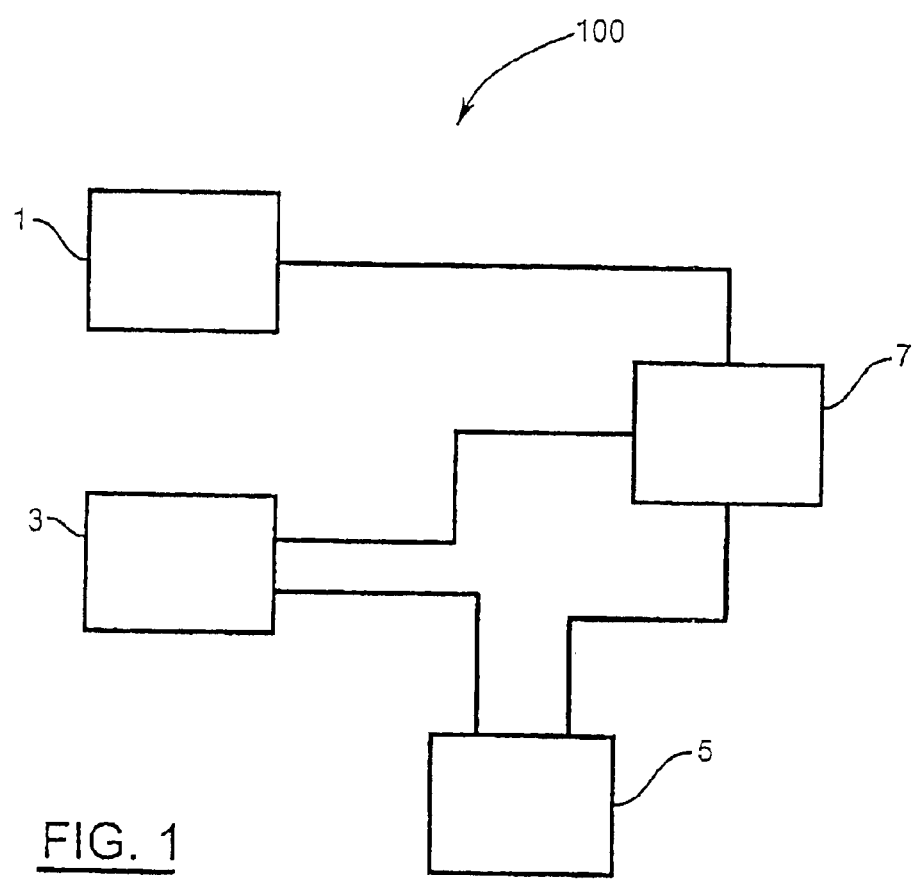
FIG. 1 is a general block diagram of an imaging apparatus according to the preferred embodiment of the present invention.

Referring to FIG. 1, an imaging apparatus 100 is used for representing and manipulating three-dimensional geometry derived from multiple two-dimensional images.

For brevity, this paragraph defines certain terms that will be used in this description. The position and orientation of a geometrical entity or physical object will be called the "pose" of the entity or object, where it is understood that the orientation of a point is arbitrary and that the orientation of a line or a plane or other special geometrical objects may be specified with only two, rather than the usual three, orientation parameters. A geometrical entity with known three-dimensional geometry will hereafter be called a "guard". A three-dimensional computer representation of the shape, surface, or volume of a geometrical entity will hereafter be called a "form". A coordinate frame, relative to a physical object that is imaged by the imaging device, will hereafter be called an "anatomical coordinate frame". A physical object, the pose of which can be determined by a computer by means of a three-dimensional tracking system, will hereafter be called a "tracked object". A physical object, the pose of which is known with respect to a tracked object, will hereafter be called a "tracked part". A tracked part that comprises a tracked object and an object that is manufactured or found will hereafter be called a "tracked tool". A tracked tool for which the pose of the tool is known in the coordinate frame of the tracked part will hereafter be called a "calibrated tracked tool". A guard, the pose of which is determined entirely or partly from the pose of a tracked tool, will hereafter be called a tool guard. A form of a tool guard will hereafter be called a "tool form". An image that is produced by an imaging system, where the imaging system is a tracked tool, will hereafter be called a "tracked image". A projection image or a tomographic image that is substantially a product of imaging geometry only, and not of artifacts or distortions introduced by the imaging system, whether calculated from geometry or calculated by processing an image derived from an imaging system, will be called a "geometrically corrected image". An image for which the surface of image creation is known with respect to the coordinate frame of a tracked part will be called a "calibrated image". An image that is the projection of one or more forms, each of which represents the geometry of a guard, onto a second two-dimensional image, will be called a "guidance image". Tracking that occurs on a time scale short enough that significant changes in the pose of a tracked object have not occurred will hereafter be called "real-time tracking". The terms defined in this paragraph are for brevity only and are not intended to restrict the principles described herein exclusively to medical applications or to any other specific application.

Referring to the Figures, like elements will be referenced with the same reference numerals from Figure to Figure, and the description of previously introduced elements will not be repeated, except to the extent required to understand the principle being discussed.

Referring to FIG. 1, an image acquisition, object tracking and integration apparatus 100 has a tracking system 1, imaging system 3, communication system 5 and integration system 7. The tracking system 1 locates objects in 3-dimensions and determines their respective poses. The imaging system 3 acquires images of objects (see FIGS. 2 and forward). Among other things, the integration system 7 correlates 3-dimensional poses captured at different times or using different capture means. The user communication system 5 provides information, such as images, sounds, or control signals to the user or other automated systems, such as a robotic control system, not shown. Two image ca techniques in common use are X-ray imaging and ultrasound imaging. The preferred embodiment is described with reference to X-ray imaging, but the principles described herein apply equally to any means of acquiring two-dimensional images and are not limited to X-ray imaging or ultrasound imaging or computed tomography or magnetic resonance imaging or any other specific means of acquiring images. Images can also be acquired by simply retrieving a digital file with the requisite information from storage on a computer readable medium.

Figure 2:
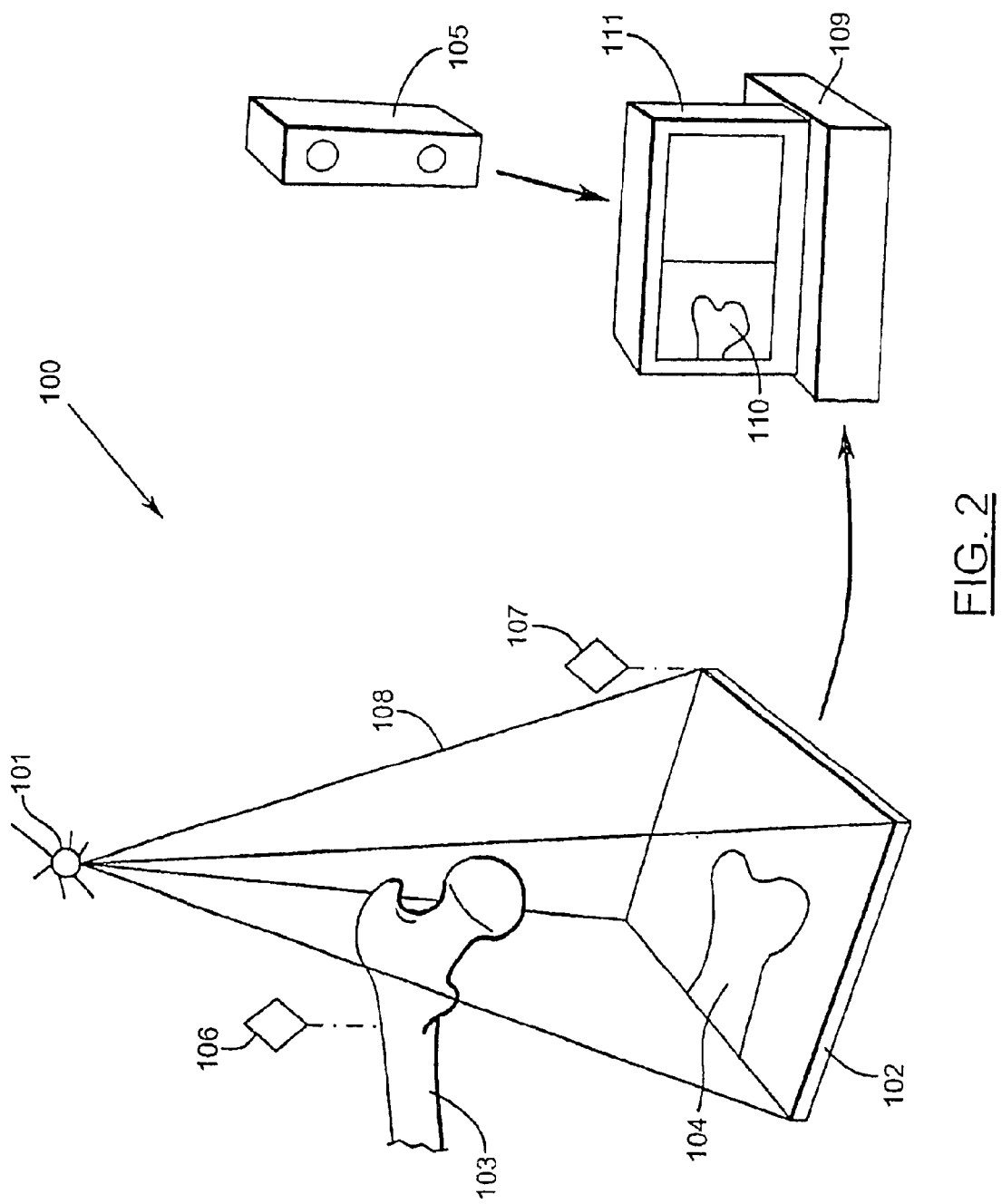
FIG. 2 is a perspective view of the imaging apparatus of FIG. 1 imaging an object from a first perspective and displaying the image.

Referring to FIG. 2, the apparatus 100 captures a first X-ray image 110. The image 110 is created by photons emitted by electromagnetic source 101 that are detected by calibrated X-ray detector 102. The electromagnetic source 101 and detector 102 form an example of an imaging system 3 of FIG. 1. Photons that are directed at object 103 are attenuated, producing a variable X-ray photon density 104 on the detector 102. The variable photon density can be transduced and communicated to computer 109 as first image 110. The computer 109 can store the first image 110 on a hard disk or other storage means. The first image 110 can be displayed on monitor 111. The monitor forms an example of the communications system 5 of FIG. 1.

In the preferred embodiment, tracking system 1 has a sensor 105 and a series of tracked parts, e.g. tracked part 106. The tracked parts utilize infrared transmitters, while the sensor 105 is an infrared sensor. The tracking system 1 determines a first pose of first tracked part 106 that is rigidly associated with the object 103 and determines a second pose of a second tracked part 107 that is rigidly associated with the detector 102. The first pose and the second pose are determined more or less simultaneously at the time that the first image 110 is captured. The tracking system 1 communicates the first pose and the second pose to the computer 109. In an alternative embodiment, the tracking system 1 determines the first pose with respect to the second pose and transmits that information to the computer 109. Examples of commercially available units that can form the basis of a tracking system 1 are the OptoTrak™ and Polaris™, manufactured by Northern Digital Incorporated, Waterloo, Canada, and various electromagnetic systems such as those made by Ascension Technology Corporation of Burlington, Vt. and Polhemus Incorporated of Colchester, Vt.

Coordinate frame 108 of the calibrated X-ray detector 102 relates the detector 102 to the electromagnetic source 101 in the coordinate frame of the second tracked part 107. In the preferred embodiment, this relation is computed by rigid transformations between coordinate frames. For example, let the pose of the calibrated X-ray detector 102 relative to the tracking system 1 be represented as a rotation $R_{102}$ followed by a translation $t_{102}$. If the coordinate of a point P is known in the coordinate frame of the calibrated X-ray detector 102 as $P_{102}$, the coordinate of the point P in the coordinate frame of the tracking system 1 can be computed as $P_1 = R_{102} * P_{102} + t_{102}$. Similarly, the pose of the first tracked part 106 relative to the tracking system 1 can be represented as a rotation $R_{106}$ followed by a translation $t_{106}$ and thus the coordinate of the point P in the coordinate frame of the first tracked part 106 can be computed as $P_{106} = R_{106}^{-1} * (P_1 - t_{106})$, where $R_{106}^{-1}$ is the inverse of $R_{106}^-$. By such calculations, the pose of the electromagnetic source 101 in the coordinate frame of the calibrated X-ray detector 102 and any point on the surface of the calibrated X-ray detector 102 and any other point in the coordinate frame 108 can be calculated in the coordinate frame of the first tracked part 106.

Figure 3:
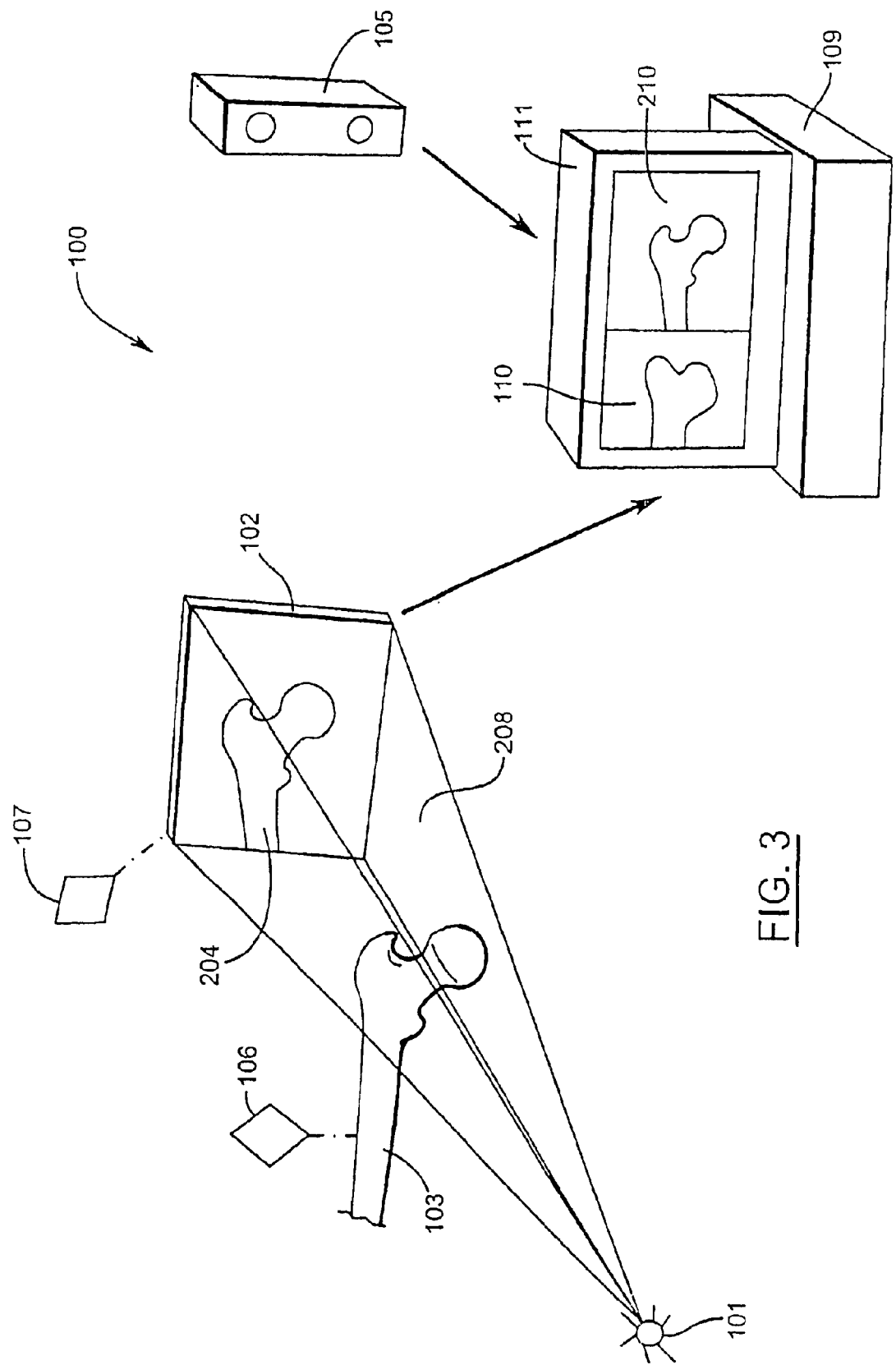
FIG. 3 is a perspective view of the imaging apparatus of FIG. 1 imaging the object of FIG. 2 from a second perspective and displaying the image.

Referring to FIG. 3, the apparatus 100 acquires a second X-ray image 210.

The second image 210 is acquired by emitting photons from electromagnetic source 101 and detecting incident photons at X-ray detector 102. Photons that encounter object 103 are attenuated, producing a variable X-ray photon density 204 on the detector 102. The variable photon density is transduced and communicated to computer 109, which displays the second X-ray image 210 on monitor 111.

Tracking system 1 next determines a third pose of first tracked part 106 that is rigidly associated with the object 103 and determines a fourth pose of second tracked part 107 that is rigidly associated with the detector 102. The third pose and the fourth pose are determined more or less simultaneously at the time that the second image 210 is captured, so that correlation of poses and other geometrical entities in terms of the coordinate frame of object 103 have little or no error. The tracking system 1 communicates the third pose and the fourth pose to the computer 109.

Second coordinate frame 208 of the calibrated X-ray detector 102 relates the detector 102 to the electromagnetic source 101 in the coordinate frame of the second tracked part 107. Calculations for points in the second coordinate frame 208 are performed analogously to the calculations for the first coordinate frame 108, so that the coordinates of any point in the second coordinate frame 108 can be calculated in the coordinate frame of first tracked part 106. In the preferred embodiment, a single detector 102 and source 101 are used for acquiring image 110, 210. It will be understood that multiple detectors 102 and source 101 could be used to acquire the images and related poses for the object 106 and detector 102. Alternatively, images 110, 210 could be acquired from storage, such as a hard disk, or scanned from film, rather than being acquired directly from the object 103. The related poses would need to be stored as well, or otherwise acquired. It will also be understood that tracking system 1 could communicate the poses of detector 102 in the coordinate frame of the first tracked part 106, or of any other coordinate frame, and that the relevant transformation from any coordinate frame to any other coordinate frame can be calculated from the relative poses of the coordinate frames.

Figure 4:
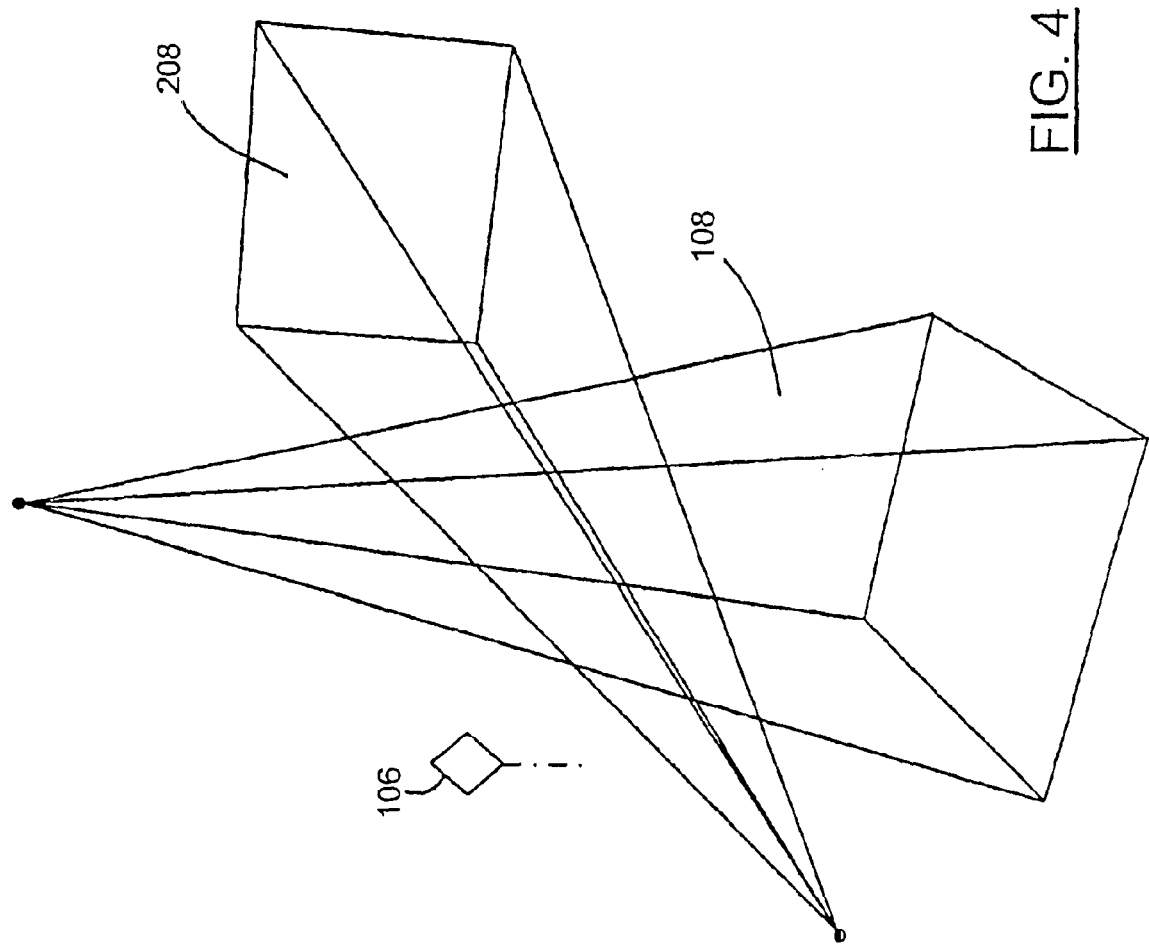
FIG. 4 illustrates projection frames for the images of FIGS. 2 and 3.

Referring to FIG. 4, knowing the first and third poses of the first tracked part 106 and second and fourth poses of second tracked part 107, the computer 109 relates the first coordinate frame 108 and the second coordinate frame 208 to the first tracked part 106. These relations are computed, as previously stated, by calculating the coordinates of a point in either coordinate frame 108 or 208 in the coordinate frame of the first tracked part 106.

Figure 5:
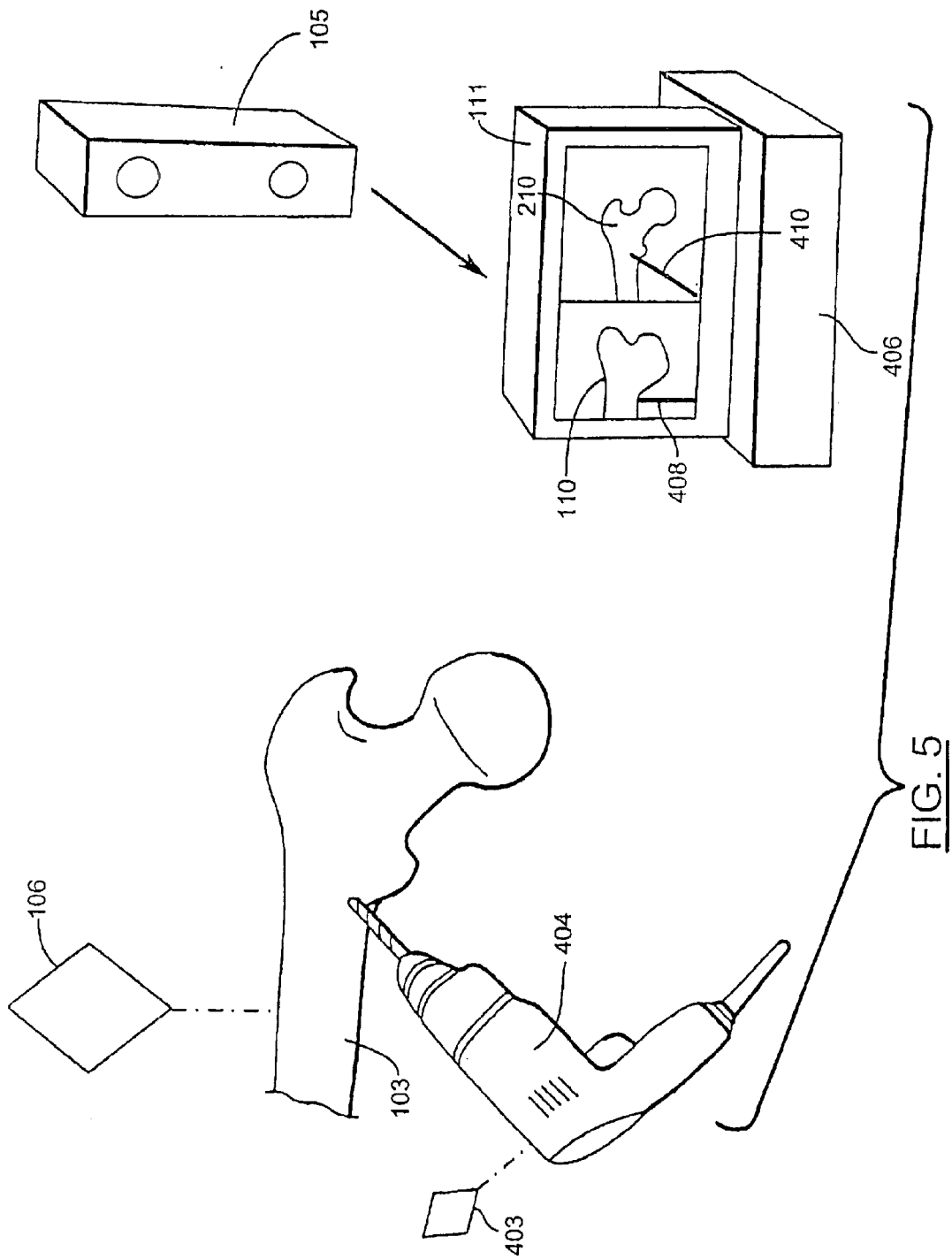
FIG. 5 is a perspective view of the imaging apparatus tracking the object of FIGS. 2 and 3, and a tracked part and tracked tool, and displaying the images of FIGS. 2 and 3, along with images of the tracked tool.

Referring to FIG. 5, tracking system 1 determines a fifth pose of first tracked part 106 that is rigidly associated with object 103. Tracking system 1 determines a sixth pose of third tracked part 403 that is rigidly associated with tracked calibrated tool 404. The fifth and sixth poses are determined more or less simultaneously. The fifth and sixth poses are communicated to computer 109. The computer 109 serves as a computing platform and has a computer program or other to control the functions described herein. It is recognized that the computer platform can take many different forms as desired by the apparatus designer. For example, without limiting the scope of the principles described herein, it can be a standalone computer, such as a personal computer, or a computer network, or it may be remotely accessible through a communications network such as the internet. Similarly, the computer program may run on a standalone computer or be distributed throughout a network, alternatively, it may run on a computer that is remotely accessible to obtain user input or input from one or more other parts of the systems 1, 3, 5, 7. The computer 109 and software together form the correlation system 7 of FIG. 1. As will be evident to those skilled in the art, other means such as a programmable logic array or dedicated hardwired computational means could be used in place of the computer 109 and computer program. It is also understood that functions of the computer 109 as described herein can be integrated or distributed as desired by the system designer, for example, separate computational means running discrete software may be provided for the tracking system 1, the imaging system 3, the correlation system 7 and the communication system 5, or the functions may be performed using computer programs running on computer 109.

The computer 109 can relate the fifth pose of first tracked part 106 and the sixth pose of the third tracked part 403. Calculations for points in the coordinate frame of the third tracked part 403 are performed analogously to the calculations for the first coordinate frame 108, so that the coordinates of any point in the coordinate frame of the third tracked part 403 can be calculated in the coordinate frame of first tracked part 106.

The computer 109 can use the first coordinate frame 108 and calibration information of the tool 404 to create a third image 408 of the tool 404. Third image 408 can be created using techniques from the field of computer graphics. For example, suppose that the form of the tool 404 is represented as a set $F_{404}$ of points in the coordinate frame of the third tracked part 403, and that the surface of detector 102 is a polygon lying in a plane known in coordinates of second tracked part 107. By means of a rigid transformation, the poses of the points in set $F_{404}$ can be computed in the coordinate frame of first tracked part 106 as set $F_{106}$. By means of another rigid transformation, the pose of electromagnetic source 101 can be determined in the coordinate frame of first tracked part 106 as point $S_{106}$ and the pose of the plane of the detector 102 can also be determined in the coordinate frame of first tracked part 106 as plane $P_{106}$. For each point in set $F_{106}$ that is distinct from point $S_{106}$ there exists a line in three dimensions that comprises each point and that also comprises point $S_{106}$. For each line, if the line intersects plane $P_{106}$ then the intersection of each line with plane $P_{106}$ can be calculated as a point lying on plane $P_{106}$. By selecting a viewpoint, and applying techniques known in the art of computer graphics, a third image 408 of the tool 404 can be created from the points lying on plane $P_{106}$. One useful viewpoint is the point $S_{106}$, because third image 408 then is a computer rendering of how tool 404 would appear in coordinate frame 108. Other useful viewpoints may also be selected, for example, to render both the form of tool 404 and the coordinate frame 108 so that the relationships between the tool and the coordinate frame are visualized. Form $F_{404}$ can be a set of line segments, known in the art as a wire-frame, or can be a set of surfaces, or can be a volume, or can be any other computer representation of tool 404 that can be rendered by means of computation.

Similarly, the computer 109 can use the fifth pose of first tracked part 106 and the sixth pose of third tracked part 403 and the second coordinate frame 208 and calibration information of the tool 404 to create a fourth image 410 of the tool 404. Fifth image 409 can be created in ways analogous to the ways in which third image 408 can be created.

In the preferred embodiment the third image 408 is merged with the first image 110 to present to the user of the apparatus 100 on the monitor 111 a visualization of the tool 404 with respect to the object 103 and the fourth image 410 is merged with the second image 210 to present to the user of the apparatus 100 on the monitor 111 a visualization of the tool 404 with respect to the object 103.

In an alternative embodiment the third image 408 is presented to the user independently of the first image 110 and the fourth image 410 is presented to the user independently of the second image 210. This alternative embodiment can be useful in understanding relations between the tool 404 and the coordinate frames 108 and 208 and the first tracked object 103.

Figure 6:
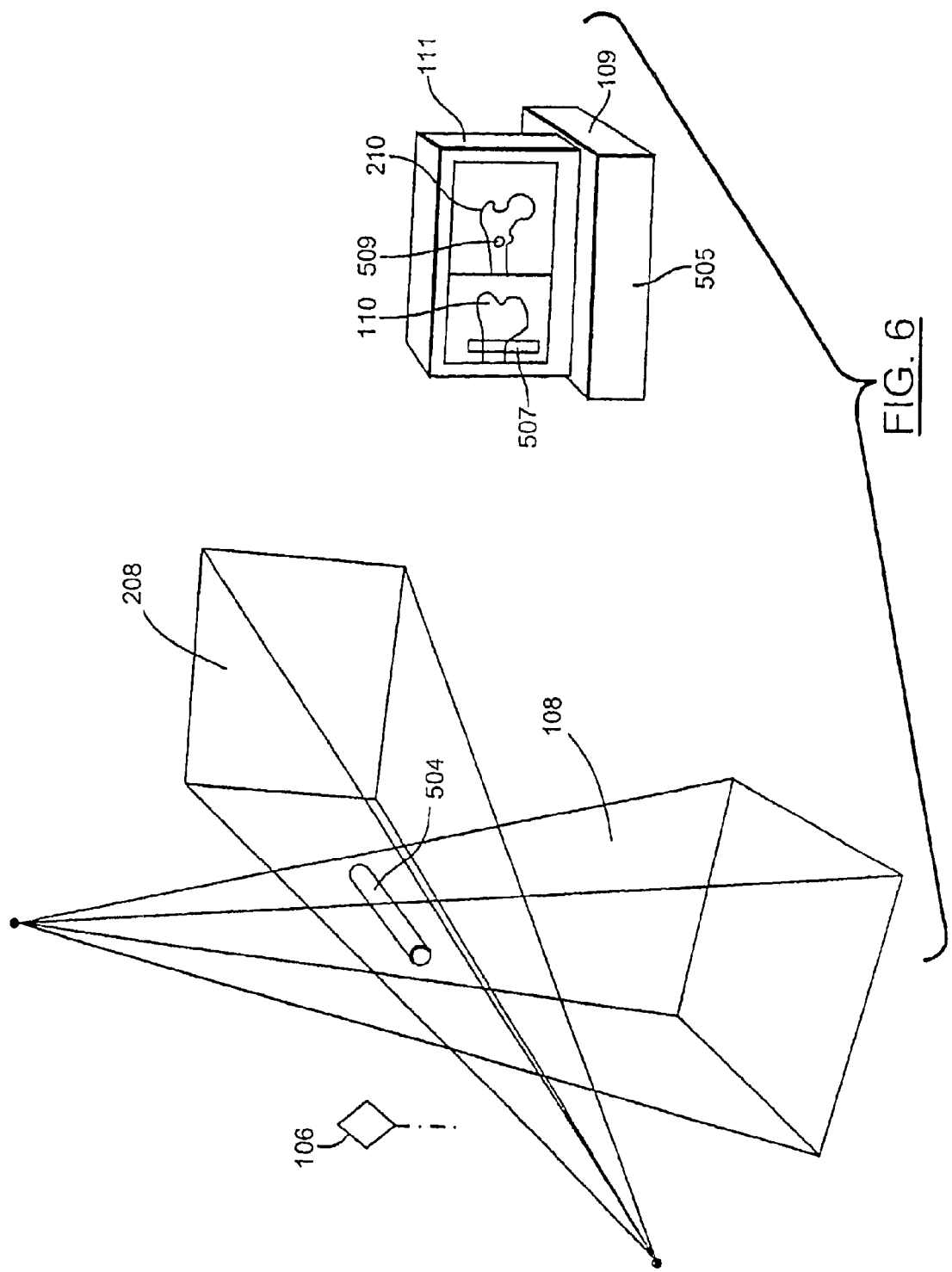
FIG. 6 is a perspective view of the imaging apparatus used to determine the placement of a guard, and displaying the images of FIGS. 2 and 3, along with images of the guard.

Referring to FIG. 6, a pose of guard 504 is determined by computer 109 in the coordinate system of first tracked part 106. Pose of the guard 504 can be adjusted by a user of computer 109.

The computer 109 can use the first pose of the tracked part 106 and second pose of second tracked part 107 and the pose of the guard 504 and other information relating to the guard 504 to create fifth image 507 of the guard 504. Fifth image 507 can be created in ways analogous to the ways in which third image 408 can be created.

Similarly, the computer 109 can use the third pose of the first tracked part 106 and the fourth pose of the second tracked part 107 and the pose of the guard 504 and other information relating to the guard 504 to create sixth image 509 of the guard 504. Sixth image 509 can be created in ways analogous to the ways in which third image 408 can be created.

In the preferred embodiment the fifth image 507 is merged with the first image 110 to present to the user of the apparatus 100 on the monitor 111 a visualization of the guard 504 with respect to the object 103, and the sixth image 509 is merged with the second image 210 to present to the user of the apparatus 110 on the monitor 111 a visualization of the guard 504 with respect to the object 103.

In an alternative embodiment the fifth image is presented to the user independently of the first image 110 and the sixth image 509 is presented to the user independently of the second image 210.

Figure 7:
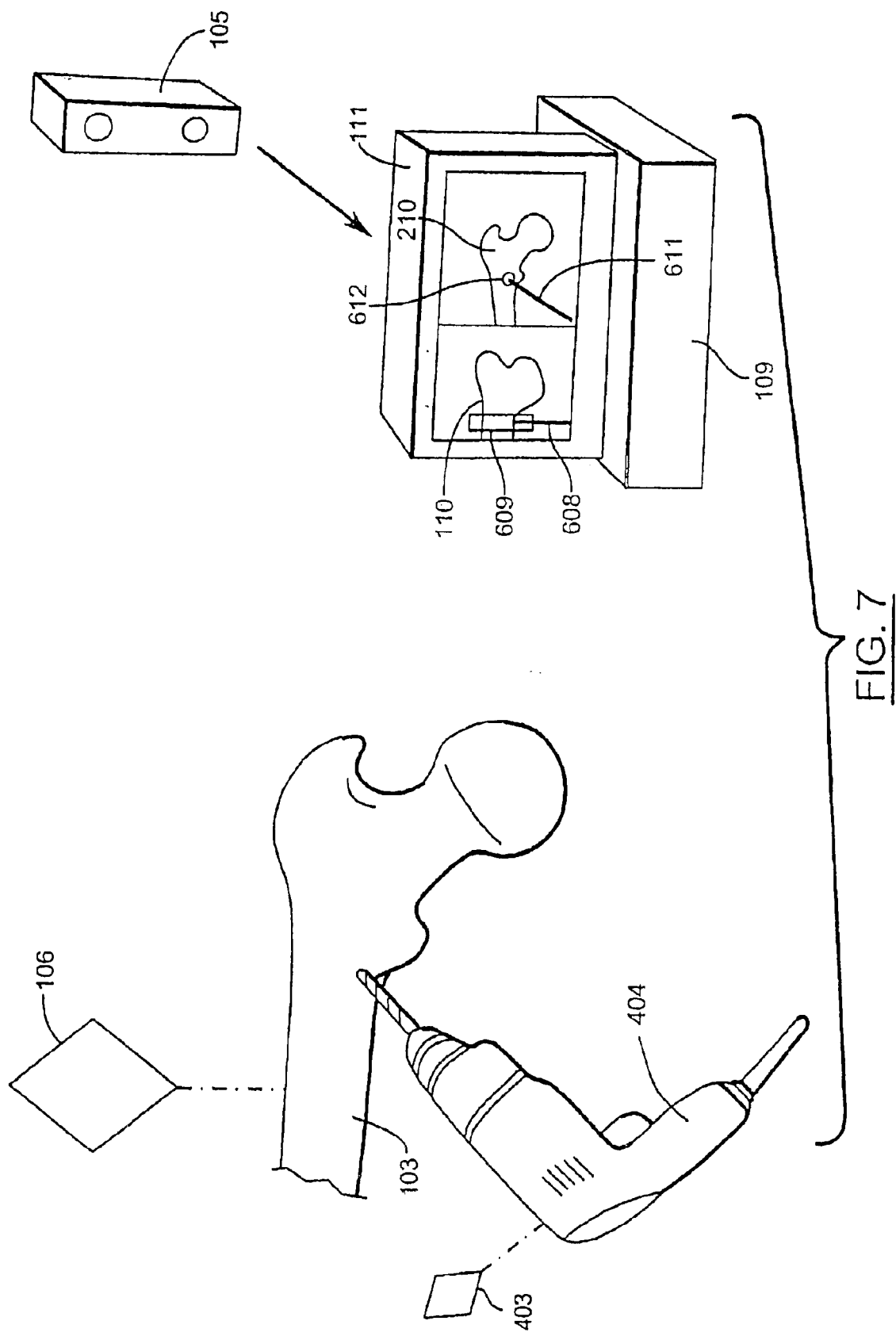
FIG. 7 is a perspective view of the imaging apparatus tracking the object of FIGS. 2 and 3, and the tracked tool of FIG. 5, and displaying the images of FIGS. 5, along with images of the guard of FIG. 6.

Referring to FIG. 7, the tracking system 1 determines the pose of first tracked part 106 that is rigidly associated with object 103. Tracking system 1 determines the pose of third tracked part 403 that is rigidly associated with tracked calibrated tool 404. The seventh and eighth poses are determined more or less simultaneously. The seventh and eighth poses are communicated to computer 109.

The computer 109 can use the seventh pose of first tracked part 106 and the eighth pose of the third tracked part 403 and the first coordinate frame 108 and calibration information of the tool 404 to create a seventh image 608 of the tool 404. The computer 109 can use the first pose of the first tracked part 106 and second pose of the second tracked part 107 and the pose of the guard 504 and other information relating to the guard 504 to create eighth image 609 of the guard 504. Eighth image 609 can be created in ways analogous to the ways in which third image 408 can be created.

Similarly, the computer 109 can use the seventh pose of first tracked part 106 and the eighth pose of the third tracked part 403 and the second coordinate frame 208 and calibration information of the tool 604 to create a ninth image 611 of the tool 404. The computer 109 can use the first pose of the first tracked part 106 and the second pose of the second tracked part 107 and the pose of the guard 504 and other information relating to the guard 504 to create tenth image 612 of the guard 504. Tenth image 612 can be created in ways analogous to the ways in which third image 408 can be created.

In the preferred embodiment said first and second and seventh through tenth images 110, 210, 608, 609, 611, 612 are merged in combinations to present to the user of the apparatus 100 on the monitor 111 a visualization of the tool 404 with respect to the object 103 and the guard 504. For example, the first and seventh and eighth images 110, 608, 609 can be merged to create a first visualization of the tool 404 with respect to the object 103 and the guard 504. The second and ninth and tenth images 210, 611, 612 can be merged to create a second visualization of the tool 404 with respect to the object 103 and the guard 504. Alternatively, the seventh and eighth images 608, 609 images can be merged to create a third visualization of the tool 404 with respect to the guard 504. Similarly, the ninth and tenth images 611, 612 can be merged. By this means the user is presented with a multiplicity of visualizations that facilitate the user in guiding the tracked calibrated tool 404 with respect to the object 103 and the guard 504.

In the preferred embodiment the user is further provided with graphical and numerical information relating geometric measurements between the tracked calibrated tool 604 and the guard 504. For example, tracked calibrated tool 604 may be a sharp surgical instrument with a substantially cylindrical shaft and guard 504 may represent an anatomical plane. The distance from the tip of tracked calibrated tool 604 to the plane of guard 504 can be calculated, as can the angle between the axis of the cylindrical shaft of tracked calibrated tool 604 and the plane of guard 504. The distance and angle can be calculated as absolute values or they can be calculated as signed values. The distance and angle can be represented numerically, for example as a distance in millimeters and an angle in degrees. The distance and angle can be represented graphically on monitor 111, for example the distance as a bar of varying length and the angle as a pie-shaped wedge of varying angle. In the preferred embodiment the user is provided with graphical and numerical information that aids the user in relating the pose of the tracked calibrated tool 604 to the pose of the guard 504.

The preferred embodiment has been described with reference to projection images created by X-ray attenuation and detection. The principles apply as well to calibrated tomographic images, for which the poses of the surfaces of image creation are known in the coordinate frames of the respective tracked parts. For tomographic images, which may not have an associated focus point, preferred points of view may include points normal to one or more of the planes of the tomographic images, or points oblique to the normals of one or more of the planes of the tomographic images. Both projection and tomographic images may be rendered using computer graphics methods as opaque, translucent, transparent or volume-rendered images, among many possible ways of rendering images.

The apparatus 100 has: a tracking system 1 tracking a tracked object, an imaging system 3, and operates with a tool 404. The imaging system 3 creates a calibrated, geometrically corrected two-dimensional image 110, 210. The correlation system 7 can receive instructions from a practitioner to create, destroy, and edit the properties of a guard. The communications system 5 displays images and calculations useful to a practitioner. The methods employed can determine geometrical relations between guards and/or present to a practitioner projections of forms of guards. An especially useful form is the form of a tracked tool.

The apparatus 100 has tracking system 1 that tracks one or more physical objects 103 such that the pose of physical object 103 is determined by the tracking system 1. The object 103 thus becomes a tracked object 103. The tracking system 1 tracks the tracked object by tracking one or more physical objects 106 that is attached to tracked object 103. The attached object is thus a tracked part 106. The tracking system 1 operates in one or more coordinate frame that is fixed with respect to a tracked part. The fixed coordinate frame is called an anatomical coordinate frame. The imaging system 3 creates calibrated, geometrically corrected two-dimensional images of one or more physical objects, either by projection or tomography. A calibrated image is a tracked image for which the pose of the surface of image creation is the coordinate frame of the tracked part. A geometrically corrected image is an image in which artifacts or distortions introduced by the imaging system have been corrected. One or more tracked tools that is not a tracked imaging system may be tracked by the tracking system 1. Examples of tracked tools are drills, probes, saws, guides, probes, or other physical objects that a practitioner can directly or indirectly manipulate. The tracking system 1 determines the pose of one or more tracked objects based on the pose information provided by the tracking system 1, where the tracked objects include: one or more tracked parts 107, all or some of each part 107 is imaged in a calibrated, geometrically corrected tracked image; one or more tracked imaging system 3, each of which produces a calibrated, geometrically corrected tracked image 110, 210; and one or more tracked tool 404. In the preferred embodiment there can be a plurality of tracked parts 107, tracked images 110, 210, and tracked tools 404. Some or all of the determination functions may be performed by the tracking system 1 utilizing software on the computer 109, which computer 109 and software form part of the tracking system 1 for this purpose.

The imaging system 3 creates calibrated, geometrically corrected images from each detector 102 and source 101, whether by using prior information or by using information derived from the images. Some or all of the calibration and geometric correction may be performed by the imaging system 3 utilizing software on the computer 109, which computer 109 and software form part of the imaging system 3 for this purpose.

Figure 8:
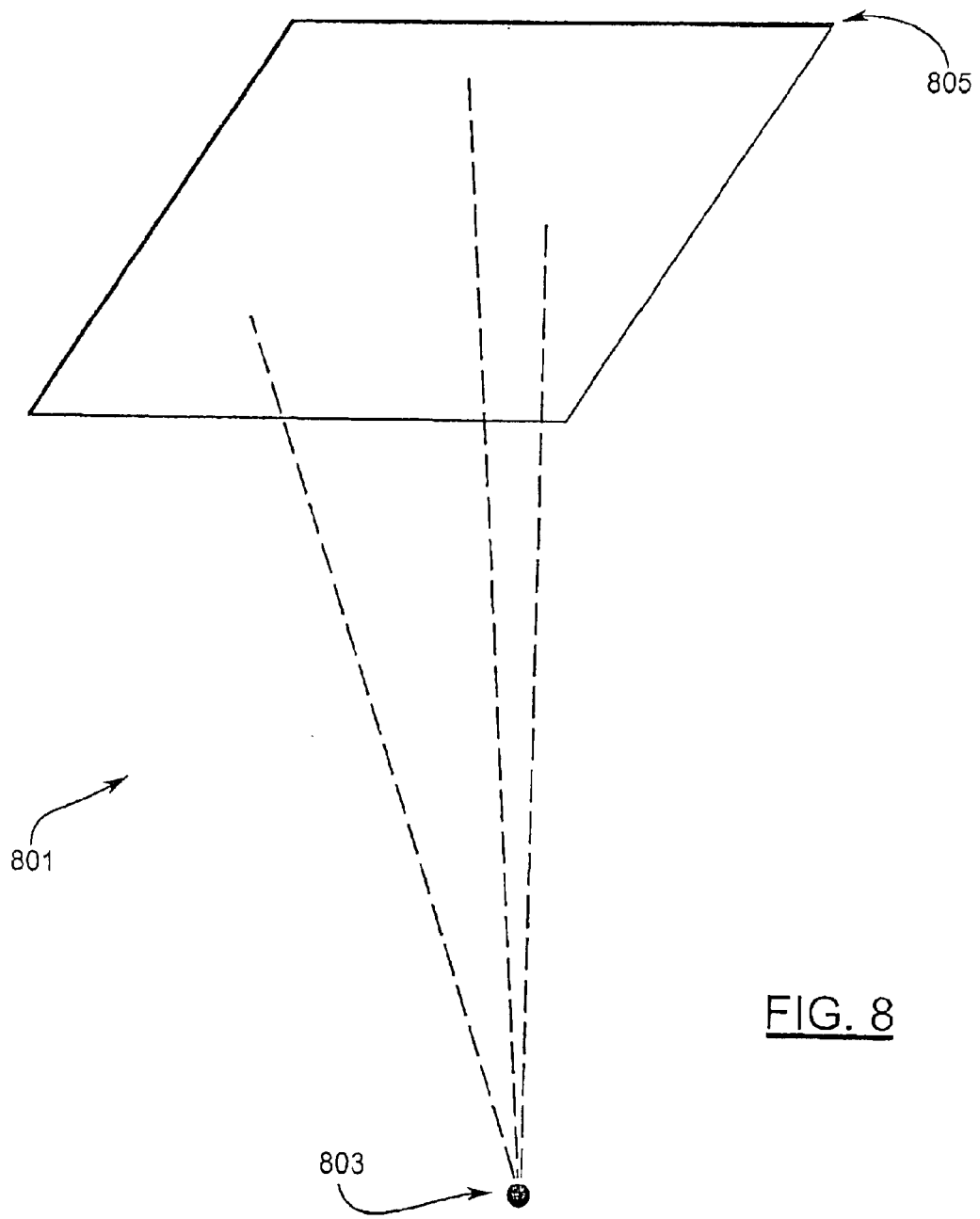
FIG. 8 illustrates a virtual imaging system employed in the imaging apparatus of FIG. 1.

Referring to FIG. 8, the communication system 5 generates two or more two-dimensional images from one or more points of view by means of a virtual imaging system 801. One of those points of view may be from the source of projected rays for projection image, where the virtual imaging system has a virtual source 803 of rays that project to a virtual surface of creation 805. As a further example, one of those points of view may be perpendicular to the surface of the image for tomographic images, where a virtual imaging system (not shown) is a computer model of the device that forms tomographic images. In the preferred embodiment a generated image is computed by a projection process or by a tomographic process. Included among those processes are perspective projection or orthographic projection or tomographic slicing among many projective mappings. One useful point of view is the pose of the X-ray source of a fluoroscopic imaging system. Some or all of the image generation may be performed by the communication system 5 utilizing software on the computer 109, which computer 109 and software form part of the communication system 5 for this purpose.

The correlation system 7 transforms an anatomical coordinate frame to another coordinate frame, the latter of which may be a distinct anatomical coordinate frame or any other coordinate frame.

The correlation system 7 can add and edit at least one guard in a known coordinate frame. In the preferred embodiment the correlation system 7 can receive directions from the practitioner or another person to add, move, or otherwise edit a guard in the anatomical coordinate frame correlated with a first calibrated, geometrically corrected image and simultaneously or successively add, move, or otherwise edit the guard in the anatomical coordinate frame correlated with a second calibrated, geometrically corrected image. In the preferred embodiment the correlation system 7 can also be directed to automatically deduce the pose of a guard from the calibrated, geometrically corrected images. The pose of a guard is preferably calculated in a third abstract coordinate frame, to which the first anatomical coordinate frame and the second anatomical coordinate frame can be transformed.

The correlation system 7 calculates a guidance image. In the preferred embodiment the image is a perspective projection, the second image is a calibrated, geometrically corrected image, the surface on which the image is created is the surface of an imaging system that corresponds to said calibrated, geometrically corrected image, and the guidance image is created so that geometry of the guard appears to be superimposed upon said second image. The resulting guard image is a computer representation of an image that might result from physical objects, which have the geometry of the forms of guards, being physically present during the process of image formation. The computer representation may include color, or other effects that are not physically possible to produce, in order to present the skilled practitioner or other person with information that clearly distinguishes the forms from said two-dimensional image.

The communication system 5 displays one or more guard images.

The communication system 5 displays the guard images sufficiently often to serve the purposes of guidance. This can be real-time image guidance.

The correlation system 7 calculates and the communication system 5 displays three-dimensional distances and angles between guards, particularly guards and tool forms. This provides relative pose information to the practitioner. This is real-time servo guidance. The communication system 5 can provide distance and angle information in many different ways. For example, it can be provided to the practitioner by means of the monitor 111 displaying numerical data or graphical data, or through audio feedback with sounds indicating "too high", "too low", "too close" or other such information. As a further example, it can be provided to a robotic control system for automated guidance of tools.

The apparatus 100 can be used in many ways to improve three-dimensional guidance from multiple two-dimensional images. In one use a practitioner skilled in the art of making fluoroscopic images of human anatomy can make two or more images of an anatomical site, such as a hip that had been fractured. A practitioner skilled in the art of surgery can add guards to the displays and use them to estimate the three-dimensional geometry of the bones, and add further guards that represent the intended three-dimensional path of one or more drill holes. The surgeon can then use a tracked tool that is a drill to drill the planned hole(s) while the apparatus 100 displays on the monitor 111 both graphically and numerically the deviations in distance and angle between the planned and actual hole(s).

The apparatus 100 improves three-dimensional guidance by introducing two-dimensional projections of one or more virtual objects of known three-dimensional geometry, the pose of each virtual object is known in a coordinate frame fixed relative to one or more physical objects that are imaged by an imaging device.

The apparatus 100 improves three-dimensional guidance from two-dimensional images by uniting two-dimensional projections of one or more forms with one or more tracked images, preferably by means of real-time tracking The apparatus 100 permits a practitioner to: derive guards, either automatically or by directing a computer, from two or more tracked images; observe images that include projections of the forms of tracked tools and of guards; and to direct a computer to report the three-dimensional relationships between guards.

The apparatus 100 provides a practitioner with a computer simulation of an arrangement of geometrical and physical objects that, in previous uses of multiple two-dimensional images, have relied primarily on the skill of the practitioner in interpreting the images.

The apparatus 100 is an improvement on existing systems as it permits a practitioner to determine one or more guards, which are three-dimensional geometrical entities defined and edited in an anatomical coordinate frame. As an illustrative example a skilled practitioner might add to an anatomical coordinate frame a guard that is a hemisphere, and might further edit the pose and radius of the hemisphere so that the projection of the form of the guard closely corresponds in two or more calibrated, geometrically corrected images to the projected images of the articular surface of the femoral head. The practitioner might then observe the calculated distance between the guard of the drill and the guard of the hemisphere, as well as observing the projections of the tool form of the guard associated with the drill and the guard of the hemisphere united with the calibrated, geometrically corrected images. The skilled practitioner might understand thereby the three-dimensional relationship between the tip of the drill and the articular surface of the femoral head.

It will be understood by those skilled in the art that this description is made with reference to the preferred embodiment and that it is possible to make other embodiments employing the principles of the invention which fall within its spirit and scope as defined by the following claims.

We claim:

1. A method of surgical navigation, the method comprising the steps of:
    acquiring a first image of part of a patient on a first surface of creation wherein the image is captured using a first imaging system;
    acquiring a first pose of the part of the patient when the part of the patient is in substantially the same pose that the part is in when the first image is captured;
    acquiring a first pose of the surface of creation with respect to the part of the patient when the part of the patient and the first imaging system are in substantially the same pose with respect to one another that the part of the patient and the first image are in when the first image is captured; and
    setting a first pose of a virtual guard with respect to the part of the patient as if the part of the patient is positioned with respect to the first virtual surface of creation in the same geometric relationship that the part of the patient has with respect to the first surface of creation.

2. The method of claim 1 further comprising the steps of:
    acquiring a second image of the part of the patient on a second surface of creation wherein the image is captured using a second imaging system;
    acquiring a second pose of the part of the patient when the part of the patient is in substantially the same pose that the part is in when the second image is captured;
    acquiring a second pose of the second surface of creation with respect to the part of the patient when the part of the patient and the second imaging system are in substantially the same pose with respect to one another that the part of the patient and the second image are in when the second image is captured;
    setting a second pose of a second virtual surface of creation with respect to the part of the patient as if the part of the patient is positioned with respect to the second virtual surface of creation in the same geometric relationship that the part of the patient has with respect to the second surface of creation; and
    setting a second pose of the virtual guard with respect to the second virtual surface of creation.

3. The method of claim 1 wherein the imaging system is a projective imaging system.

4. The method of claim 3 further comprising the steps of:
    acquiring a pose of the first imaging system with respect to the first surface of creation;
    setting a first pose of a first virtual imaging system with respect to the first virtual surface of creation; and
    projecting a first virtual image of the virtual guard onto the first virtual surface of creation using the first virtual imaging system.

5. The method of claim 2 wherein the second imaging system is a projective imaging system.

6. The method of claim 5 further comprising the steps of:
    acquiring a pose of the second imaging system with respect to the second surface of creation;
    setting a second pose of a second virtual imaging system with respect to the second virtual surface of creation; and
    projecting a second virtual image of the virtual guard onto the second virtual surface of creation using the second virtual imaging system.

7. A method of surgical navigation, the method comprising the steps of:
    acquiring a first image of part of a patient on a first surface of creation wherein the image is captured using a first imaging system;
    acquiring a first pose of the part of the patient when the part of the patient is in substantially the same pose that the part is in when the first image is captured;
    acquiring a first pose of the surface of creation with respect to the part of the patient when the part of the patient and the first imaging system are in substantially the same pose with respect to one another that the part of the patient and the first image are in when the first image is captured;
    acquiring a first pose of a tool; and
    setting a first pose of a virtual form of the tool with respect to the part of the patient as if the part of the patient is positioned with respect to the first virtual surface of creation in the same geometric relationship that the part of the patient has with respect to the first surface of creation.

8. The method of claim 7 wherein the first imaging system is a projective imaging system.

9. The method of claim 8 further comprising the steps of:
    acquiring a pose of the first imaging system with respect to the first surface of creation;
    setting a first pose of a first virtual imaging system with respect to the first virtual surface of creation; and
    projecting a first virtual image of the virtual form of the tool onto the first virtual surface of creation using the first virtual imaging system.

10. A method of surgical navigation, the method comprising the steps of:
acquiring a first image of part of a patient on a first surface of creation wherein the image is captured using a first imaging system;
acquiring a first pose of the part of the patient when the part of the patient is in substantially the same pose that the part is in when the first image is captured;
acquiring a first pose of the surface of creation with respect to the part of the patient when the part of the patient and the first imaging system are in substantially the same pose with respect to one another that the part of the patient and the first image are in when the first image is captured;
setting a first pose of a first virtual surface of creation with respect to the part of the patient as if the part of the patient is positioned with respect to the first virtual surface of creation in the same geometric relationship that the part of the patient has with respect to the first surface of creation;
setting a first pose of a first virtual guard with respect to a first virtual surface of creation;
acquiring a first pose of a tool; and
setting a first pose of a virtual form of the tool with respect to the part of the patient as if the part of the patient is positioned with respect to the first virtual surface of creation in the same geometric relationship that the part of the patient has with respect to the first surface of creation.

11. The method of claim 10 wherein the first imaging system is a projective imaging system.

12. The method of claim 11 further comprising the steps of:
acquiring a pose of the first imaging system with respect to the first surface of creation;
setting a first pose of a first virtual imaging system with respect to the first virtual surface of creation; and
projecting a first virtual image of the virtual form of the tool onto the first virtual surface of creation using the first virtual imaging system.

13. The method of claim 11 further comprising the steps of:
acquiring a pose of the first imaging system with respect to the first surface of creation;
setting a first pose of a first virtual imaging system with respect to the first virtual surface of creation; and
projecting a first virtual image of the virtual guard onto the first virtual surface of creation; and
projecting a first virtual image of the virtual guard onto the first virtual surface of creation using the first virtual imaging system.

14. The method of claim 10 further comprising:
acquiring a pose of the tool on an ongoing basis;
acquiring a pose of the part of the patient on an ongoing basis; and
resetting the first pose of the virtual form of the tool on an ongoing basis to compensate for changes of the pose of the tool with respect to the part of the patient.

15. The method of claim 1, 7 or 10 further comprising the step of storing the acquired images on a computer readable medium after the images are acquired.

16. The method of claim 1, 7 or 10 further comprising the step of displaying each acquired image together with one or more of the virtual images created from the same projected perspective.

17. The method of claim 1, 7 or 10 further comprising the step of displaying one or more virtual images, where multiple virtual images are created from the same projected perspective, without displaying an acquired image.

18. The method of claim 1 further comprising performing the steps of claim 1 for a plurality of images of the part of the patient.

19. The method of claim 1 further comprising performing the steps of claim 1 for a plurality of guards.

20. The method of claim 7 further comprising the steps of claim 7 for a plurality of tools.

21. The method of claim 10 further comprising the steps of claim 10 for a plurality of guards.

22. The method of claim 21 further comprising the steps of claim 10 for a plurality of tools.

23. The method of claim 10 further comprising the steps of claim 10 for a plurality of tools.

24. The method of claim 20, 22 or 23 further comprising the step of calculating relative pose information of a tool and another tool.

25. The method of claim 10 further comprising the step of calculating relative pose information of the tool and the guard.

26. The method of claim 25 further comprising the step of displaying relative pose information of the tool and the guard.

27. The method of claim 26 wherein the relative pose information is displayed by displaying images of the tool and guard.

28. The method of claim 26 wherein the relative pose information is displayed audibly.

29. The method of claim 26 wherein the relative pose information is displayed visually in the form of numerical data.

30. The method of claim 26 wherein the relative pose information is displayed graphically.

31. The method of claim 22 further comprising the step of calculating relative pose information of one or more tools and one or more guards.

32. The methods of claims 7 or 10 wherein the tool is selected from a group consisting of drills, probes, saws, guides, probes, or another physical objects that a practitioner can directly or indirectly manipulate.

33. The method of claim 20, 22 or 23 wherein tools are selected from a group consisting of drills, probes, saws, guides, probes, or another physical objects that a practitioner can directly or indirectly manipulate.

34. The method of claim 19 or 21 wherein guards are selected from a group consisting of drill holes, probe holes, saw cuts, guide holes, probe holes, or another three-dimensional computer representation of a geometrical entity.

35. The method of claim 1, 7 or 10 wherein images are acquired by capturing the images from the patient using an imaging system.

36. The methods of claim 35 wherein the imaging system is an X-ray system.

37. The methods of claim 35 wherein the imaging system is an ultrasound system.

38. The method of claim 1, 7 or 10 wherein images are acquired by retrieving from a computer readable file previously captured images.

39. The method of claim 1, 7 or 10 wherein poses are acquired by tracking poses using a tracking system.

40. The methods of claim 39 wherein the tracking system transmits signals from items and receives transmitted signals at a sensor, and the tracking system determines poses from the received transmitted signals.

41. The method of claim 1, 7 or 10 wherein poses are acquired by retrieving from a computer readable file previously tracked poses.

42. The method of claim 1, 7 or 10 wherein poses are acquired by retrieving from a computer readable file previously tracked poses.

43. The method of claim 1, 7 or 10 wherein image are geometrically corrected to represent substantially a product of projective geometry only, and not of artifacts or distortions introduced by an imaging system, whether calculated from geometry or calculated by processing an image derived from an imaging system.

44. An apparatus for use in surgical navigation, the apparatus comprising:
- a tracking system for tracking objects,
- an imaging system for acquiring 2-dimensional images of objects,
- a communication system for receiving input from and providing output to a user,
- an integration system for correlating images acquired at different times or using different means of acquisition,
- a computing platform, and
- computer program means on computer readable media for use on the computer platform, the computer program means comprising:
    - instructions to carry out the steps of the method of claim 1, 7 or 10 using the tracking system, imaging system, communication system and integration system.

45. The apparatus of claim 44 wherein the tracking system comprises: one or more transmitters on each object for transmitting a signal, and one or more sensors for receiving transmitted signals, the transmitter determining a pose of an object using the received transmitted signals.

46. A computer program on a computer readable medium for use on a computer platform in association with a tracking system for tracking objects, an imaging system for acquiring 2-dimensional images of objects, a communication system for receiving input from and providing output to a user, an integration system for correlating images acquired at different times or using different means of acquisition, the computer program comprising:
- instructions to carry out the steps of the method of claim 1, 7 or 10 using the tracking system, imaging system, communication system and integration system.

47. An apparatus for use in surgical navigation, the apparatus comprising:
- a tracking system for tracking objects,
- an imaging system for acquiring 2-dimensional images of objects,
- an integration system for correlating images acquired at different times or using different means of acquisition,
- wherein the imaging system acquires a first image of part of a patient on a first surface of creation, the image is captured using a first imaging system,
- the tracking system acquires a first pose of the part of the patient when the part of the patient is in substantially the same pose that the part is in when the first image is captured,
- the tracking system acquires a first pose of the first imaging system with respect to the part of the patient when the part of the patient is in substantially the same pose that the part is in when the first image is captured,
- the tracking system acquires a first pose of the surface of creation with respect to the part of the patient when the part of the patient and the first imaging system are in substantially the same pose with respect to one another that the part of the patient and the first image are in when the first image is captured,
- the integration system sets a first pose of a first virtual imaging system with respect to a first virtual surface of creation,
- the integration system sets a first pose of a virtual guard with respect to the part of the patient as if the part of the patient is positioned with respect to the first virtual imaging system and the first virtual surface of creation in the same geometric relationship that the part of the patient has with respect to the first imaging system and the first surface of creation,
- the integration system projects a first virtual image of the guard onto the first virtual surface of creation using the first virtual imaging system.

48. An apparatus for use in surgical navigation in association with an acquired first image of part of a patient on a first surface of creation, the image captured using a first imaging system; an acquired first pose of the part of the patient when the part of the patient is in substantially the same pose that the part is in when the first image is captured, an acquired first pose of the first imaging system with respect to the part of the patient when the part of the patient is in substantially the same pose that the part is in when the first image is captured, and an acquired first pose of the surface of creation with respect to the part of the patient when the part of the patient and the first imaging system are in substantially the same pose with respect to one another that the part of the patient and the first image are in when the first image is captured, the apparatus comprising:
- an integration system for correlating images acquired at different times or using different means of acquisition,
- wherein the integration system sets a first pose of a first virtual imaging system with respect to a first virtual surface of creation,
- wherein the integration system sets a first pose of a virtual guard with respect to the part of the patient as if the part of the patient is positioned with respect to the first virtual imaging system and the first virtual surface of creation in the same geometric relationship that the part of the patient has with respect to the first imaging system and the first surface of creation,
- and wherein the integration system projects a first virtual image of the guard onto the first virtual surface of creation using the first virtual imaging system.

49. An apparatus for use in surgical navigation in association with an acquired first image of part of a patient on a first surface of creation, the image captured using a first imaging system; an acquired first pose of the part of the patient when the part of the patient is in substantially the same pose that the part is in when the first image is captured, an acquired first pose of the first imaging system with respect to the part of the patient when the part of the patient is in substantially the same pose that the part is in when the first image is captured, an acquired first pose of the surface of creation with respect to the part of the patient when the part of the patient and the first imaging system are in substantially the same pose with respect to one another that the part of the patient and the first image are in when the first image is captured, and an acquired first pose of a tool, the apparatus comprising:
- an integration system for correlating images acquired at different times or using different means of acquisition,
- wherein the integration system sets a first pose of a first virtual imaging system with respect to a first virtual surface of creation, wherein the integration system sets a first pose of a virtual form of the tool with respect to the part of the patient as if the part of the patient is positioned with respect to the first virtual imaging system and the first virtual surface of creation in the same geometric relationship that the part of the patient has with respect to the first imaging system and the first surface of creation, and wherein the integration system projects a first virtual image of the tool onto the first virtual surface of creation using the first virtual imaging system.

50. An apparatus for use in surgical navigation in association with an acquired first image of part of a patient on a first surface of creation, the image captured using a first imaging system; an acquired first pose of the part of the patient when the part of the patient is in substantially the same pose that the part is in when the first image is captured, an acquired first pose of the first imaging system with respect to the part of the patient when the part of the patient is in substantially the same pose that the part is in when the first image is captured, and an acquired first pose of the surface of creation with respect to the part of the patient when the part of the patient and the first imaging system are in substantially the same pose with respect to one another that the part of the patient and the first image are in when the first image is captured, and an acquired first pose of a tool, the apparatus comprising:

an integration system for correlating images acquired at different times or using different means of acquisition, wherein the integration system sets a first pose of a first virtual imaging system with respect to a first virtual surface of creation, wherein the integration system sets a first pose of a virtual form of the tool with respect to the part of the patient as if the part of the patient is positioned with respect to the first virtual imaging system and the first virtual surface of creation in the same geometric relationship that the part of the patient has with respect to the first imaging system and the first surface of creation, wherein the integration system projects a first virtual image of the tool onto the first virtual surface of creation using the first virtual imaging system, wherein the integration system sets a first pose of a virtual guard with respect to the part of the patient as if the part of the patient is positioned with respect to the first virtual imaging system and the first virtual surface of creation in the same geometric relationship that the part of the patient has with respect to the first imaging system and the first surface of creation, and wherein the integration system projects a first virtual image of the guard onto the first virtual surface of creation using the first virtual imaging system.

* * * * *